(12) United States Patent
Feng et al.

(10) Patent No.: US 7,208,512 B2
(45) Date of Patent: Apr. 24, 2007

(54) BENZODIFURANIMIDAZOLINE AND BENZOFURANIMIDAZOLINE DERIVATIVES AND THEIR USE FOR THE TREATMENT OF GLAUCOMA

(75) Inventors: Zixia Feng, Arlington, TX (US); Mark R. Hellberg, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 296 days.

(21) Appl. No.: 10/525,410

(22) PCT Filed: Dec. 9, 2002

(86) PCT No.: PCT/US02/39316

§ 371 (c)(1),
(2), (4) Date: Jan. 26, 2005

(87) PCT Pub. No.: WO03/053436

PCT Pub. Date: Jul. 3, 2003

(65) Prior Publication Data

US 2006/0009503 A1  Jan. 12, 2006

Related U.S. Application Data

(60) Provisional application No. 60/343,378, filed on Dec. 20, 2001.

(51) Int. Cl.
*A61K 31/4178* (2006.01)
*A61K 31/4196* (2006.01)
*A61K 31/4025* (2006.01)
*C07D 233/58* (2006.01)
*C07D 249/08* (2006.01)
*C07D 405/10* (2006.01)
*C07D 405/14* (2006.01)

(52) U.S. Cl. ............. 514/397; 514/383; 514/422; 548/311.7; 548/266.4; 548/526

(58) Field of Classification Search ............ 548/311.1, 548/315.4, 347.1, 355.1, 311.7, 266.4, 526; 549/429, 460; 514/397, 383, 422
See application file for complete search history.

(56) References Cited

U.S. PATENT DOCUMENTS

| | | | |
|---|---|---|---|
| 5,011,846 A | 4/1991 | Gittos et al. | 514/294 |
| 5,290,781 A | 3/1994 | Espino et al. | 514/259 |
| 5,494,928 A | 2/1996 | Bös | 514/415 |
| 5,538,974 A | 7/1996 | Ogawa et al. | 514/253 |
| 5,561,150 A | 10/1996 | Wichmann | 514/406 |
| 5,571,833 A | 11/1996 | Kruse et al. | 514/414 |
| 5,578,612 A | 11/1996 | Macor et al. | 514/323 |
| 5,646,173 A | 7/1997 | Bös et al. | 514/411 |
| 5,652,272 A | 7/1997 | Ogawa et al. | 514/652 |
| 5,693,654 A | 12/1997 | Birch | 514/323 |
| 5,874,477 A | 2/1999 | McConnell et al. | 514/657 |
| 5,891,131 A | 4/1999 | Rajan et al. | 606/5 |
| 5,902,815 A | 5/1999 | Olney et al. | 514/285 |
| 6,107,324 A | 8/2000 | Behan et al. | 514/406 |
| 6,660,870 B1 | 12/2003 | Ruskinko et al. | 548/307.4 |
| 6,664,286 B1 | 12/2003 | May et al. | 514/415 |
| 6,696,476 B2 | 2/2004 | Chen et al. | 514/403 |
| 6,806,285 B1 | 10/2004 | May et al. | 514/416 |
| 6,884,816 B2 | 4/2005 | May et al. | 514/405 |
| 2003/0181503 A1 | 9/2003 | May et al. | 514/406 |

FOREIGN PATENT DOCUMENTS

| | | |
|---|---|---|
| CA | 2036975 | 8/1991 |
| EP | 0 771 563 B1 | 1/2003 |
| ES | 323985 | 12/1966 |
| WO | WO 92/00338 | 1/1992 |
| WO | WO 94/03162 | 2/1994 |
| WO | WO 97/35579 | 10/1997 |
| WO | WO 98/18458 | 5/1998 |
| WO | WO 98/31354 | 7/1998 |
| WO | WO 99/59499 | 11/1999 |
| WO | WO 00/12475 | 3/2000 |
| WO | WO 00/12510 | 3/2000 |
| WO | WO 00/16761 | 3/2000 |
| WO | WO 00/35922 | 6/2000 |
| WO | WO 00/44753 | 8/2000 |
| WO | WO 01/40183 | 6/2001 |
| WO | WO 01/70207 | 9/2001 |
| WO | WO 01/70223 | 9/2001 |
| WO | WO 01/70230 | 9/2001 |
| WO | WO 01/70701 | 9/2001 |
| WO | WO 01/70702 | 9/2001 |
| WO | WO 01/70745 | 9/2001 |
| WO | WO 02/098350 | 12/2002 |
| WO | WO 02/098400 | 12/2002 |
| WO | WO 02/098860 | 12/2002 |
| WO | WO 03/051291 | 6/2003 |

(Continued)

OTHER PUBLICATIONS

Levin, Leonard, "Neuroprotection in neuro-ophthalmic disease", 2000, Neuro-ophthalmology, 24, p. 383-386.*

(Continued)

*Primary Examiner*—Joseph K. McKane
*Assistant Examiner*—Karen Cheng
(74) *Attorney, Agent, or Firm*—Patrick M. Ryan

(57) ABSTRACT

The present invention provides benzodifuran imidazoline derivatives and benzofuran imidazoline derivatives for lowering intraocular pressure and providing ocular neuroprotection.

14 Claims, No Drawings

FOREIGN PATENT DOCUMENTS

| WO | WO 03/051352 | 6/2003 |
|---|---|---|
| WO | WO 03/053436 | 7/2003 |
| WO | WO 2004/019874 | 3/2004 |
| WO | WO 2004/028451 | 4/2004 |
| WO | WO 2004/054572 | 7/2004 |
| WO | WO 2004/058725 | 7/2004 |

OTHER PUBLICATIONS

Obach, R. Scott, "Drug-drug interactions", 2003, Drugs of Today, 39(5), p. 301-311.*

Boudier et al., "Structure Activity Relationships for Central and Peripheral Alpha Adrenergic Activities of Imidazoline Derivatives," *Life Sciences*, vol. 17, pp. 377-386 (1975).

Bowen et al., "Nonlinear regression using spreadsheets," *Trends in Pharmacological Sciences*, vol. 16, pp. 413-417 (1995).

Bradford et al., "A Rapid and Sensitive Method for the Quantitaion of Mircorgam Quantities of Protein Utilizing the Principle of Protein-Dye Binding," *Analytical Biochemistry*, vol. 72, pp. 248-254 (1976).

Chambers et al., Enantiospecific Synthesis and Pharmacological Evaluaion of a Series of Super-Potent, Conformationally Restricted 5-HT$_{2A2C}$ Receptor Agonists, *J. Med. Chem.*, vol. 44, pp. 1003-1010 (2001).

Chang et al., "Mechanism of the Ocular Hypotensive Action of Ketanserin," *J. of Ocular Pharmacology*, vol. 1(2), pp. 137-147 (1985).

De Vry et al., "Characterization of the Aminomethylchroman Derivative BAYx3702 as a Highly Potent 5-Hydroxytryptamine$_{1A}$ Receptor Agonist," *J. of Pharmacology and Experimental Therapeutics*, vol. 284 (3), pp. 1082-1094 (1998).

Florella et al., "The role ofo the 5-HT$_{2A}$ and 5-HT$_{2C}$ receptors in the stimulus effects of hallucinogenic drugs III: the mechanistic basis for supersensitivity to the LSD stimulus following serotonin depletion," *Psychopharmacology*, vol. 121, pp. 364-372 (1995).

Griffin et al., "Pharmacological Characterization of an FP Prostaglandin Receptor on Rat Vascular Smooth Muscle Cells (A7r5) Coupled to Phosphoinositide Turnover and Intracellular Calcium Mobilization," *J. of Pharmacology and Experimental Therapeutics*, vol. 286(1), pp. 411-418 (1998).

Gupta et al., "Therapeutic Potentials of 5-HT Receptor Modulators," *Indian J. of Pharmacology*, vol. 26, pp. 94-107 (1994).

Hoyer et al., VII. International Union of Pharmacology Classification of Receptors for 5-Hydroxytryptamine (Serotonin), *Pharmacological Reviews*, vol. 46(2), pp. 157-203 (1994).

Johnson et al., Binding to the Serotonin 5-HT$_2$ Receptor by the Enantiomers of $^{125}$I-DOI, *Neuropharmacology*, vol. 26(12), pp. 1803-1806 (1987).

Krootila et al., "Effect of Serotonin and its Antagonist (Ketanserin) in Intraocular Pressure in the Rabbit," *J. of Ocular Pharmacology*, vol. 3(4), pp. 279-290 (1987).

Lopez-Rodriguez, "Synthesis and Structure-Activity Relationships of a New Model of Arylpiperazines. 4.$^1$-(ω-(4-Arylpiperazine-1-yl)alkyl]-3-(diphenylmethylene)-2,5-pyrrolidinediones and -3-(9*H*-fluoren-9-ylidene)-2,5-pyrrolidinediones:Study of the Steric Requirements of the Terminal Amide Fragment on 5-HT$_{1A}$ Affinity/Selectivity," J. Med. Chem., 42(1):36-49 (1999).

Mallorga et al., "Characterization of serotonin receptors in the iris+ciliary body of the albino rabbit," *Current Eye Research*, vol. 6(3), pp. 527-532 (1987).

Martin et al., "The Structure and Signalling Properties of 5-HT Receptors: an endless diversity?" *Trends in Pharmaceutical Sciences*, vol. 19, pp. 2-4 (1998).

Mano et al., "The Effect of Anplag (Sarpogelate HCL), New Selective 5-HT$_2$ Antagonist on Intraocular Pressure in Rabbits," *IOVS*, vol. 36(4), S719 (1995).

May et al., "A Novel and Selective 5-HT$_2$ Receptor Agonist with Ocular Hypotensive Activity: (*S*)-(+)-1-(2-Aminopropyl)-8,9-dihydropyrano[3,2-e]indole," *J. Med. Chem.*, vol. 46, pp. 4188-4195 (2003).

May et al., "Evaluation of the Ocular Hypotensive Response of Serotonin 5-HT$_{1A}$ and 5-HT$_2$ Receptor Ligands in Conscious Ocular Hypertensive Cynomolgus Monkeys," *J. of Pharmacology and Experimental Therapeutics*, vol. 306(1), pp. 301-309 (2003).

Monte et al, "Dihydrobenzofuran Analogues of Hallucinogens. 3$^1$ Models of 4-Substituted (2,5-Dimethoxyphenyl)alkylamine Derivatives with Rigiddified Methoxy Groups," *J. Med. Chem.*, vol. 39, pp. 2953-2961 (1996).

Morin et al, "A Method to Measure Simultaneously Cyclic AMP and Inositol Phosphate Accumulationin Rat Brain Slices," *J. Of Neurochemistry*, vol. 56(4), pp. 1114-1120 (1991).

Osborne et al., "Do Beta-Adrenoceptors and Serotonin 5-HT$_{1A}$Receptors Have Similar Functions in the Control of Intraocular Pressure in the Rabbit?", *Ophthalmologica*, vol. 210, pp. 308-314 (1996).

Osborne et al., "5-Hydroxytryptamine$_{1A}$ agonists: potential use in glaucoma. Evidence from animal studies," *Eye*, vol. 14(38), pp. 454-463 (2000).

Salomon et al., "Adenylate Cyclase Assay," *Advances in Cyclic Nucleotide Research*, vol. 10, pp. 35-55 (1979).

Salomon et al., "[2] Cellular Responsiveness to Hormones and Neurotransmitters: Conversion of [$^3$H]Adenine to [$^3$H]cAMP in Cell Monolayers, Cell Suspensions, and Tissue Slices," *Methods in Enzymology*, vol. 195, pp. 22-28 (1991).

Schoeffter et al., "Inhibition of cAMP Accumulation Via Recombinant Human Serotonin 5-HT$_{1A}$ Receptors: Considerations on Receptor Effector Coupling across Systems," *Neuropharmacology*, vol. 36(4/5), pp. 429-437 (1997).

Sharif et al., "[$^3$H]AL-5848 ([$^3$H]9β-(+)-Fluprostenol). Carboxylic Acid of Travoprost (AL-6221), a Novel FP Prostaglandin o Study the Pharmacology and Autoradiographic Localization of the FP Receptor," *J. Pharm. Pharmacol.* vol. 51: pp. 685-694 (1999).

Takeda et al., "The Effect of Inplag. Novel Selective 5-HT$_2$ Antagonist on Intraocular Pressure in Glaucoma Patients," IOVS, Vo. 36(4), S734 (1995).

Tobin et al., "Evidence for the Presence of Serotonergic Nerves and Receptors in the Iris-Ciliary Body Complex of the Rabbit," *The J. of Neurosciences*, vol. 8(10), pp. 3713-3721 (1988).

Wang et al., "Effect of 5-methylurapidil, and α$_{1a}$_adrenergic antagonist and 5-hydroxytryptamine$_{1a}$ agonist on aqueous humor dynamics in monkeys and rabbits," *Current Eye Research*, vol. 16(8), pp. 769-775 (1997).

Wang et al., "Effect of Oxymetazoline on Aqueous Humor Dynamics and Ocular Blood Flow in Monkeys and Rabbits," *Archives of Ophthalmology*, vol. 111, pp. 535-538 (1993).

Wang et al., "Effect of p-MPPI Hydrochloride (p-MPPI) Applied Before 5-Methylurapidil (5-MU) on Intraocular Pressure (IOP) in Normal Monkeys," IVOS, 39(4), S488 (1998).

Zifa et al., "5-Hydroxytryptamine Receptors," *Pharmacological Reviews*, vol. 44(3), pp. 401-458 (1992).

* cited by examiner

BENZODIFURANIMIDAZOLINE AND BENZOFURANIMIDAZOLINE DERIVATIVES AND THEIR USE FOR THE TREATMENT OF GLAUCOMA

This application claims priority to international application PCT/US02/39316, filed Dec. 9, 2002, which claims priority from U.S. Provisional Application, Ser. No. 60/343,378, filed Dec. 20, 2001.

BACKGROUND OF THE INVENTION

1. Field of the Invention

The present invention relates to the field of glaucoma treatment and ocular neuroprotection. More particularly, the present invention provides novel compounds, compositions and methods for treating glaucoma, lowering intraocular pressure and providing neuroprotection.

2. Description of the Related Art

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be at high risk for the eventual development of the visual loss associated with glaucoma. Some patients with glaucomatous field loss have relatively low intraocular pressures. These so called normal tension or low tension glaucoma patients can also benefit from agents that lower and control IOP. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility.

Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

Serotonin (5-hydroxy tryptamine; 5HT) is an endogenous biogenic amine with a well defined neurotransmitter function in many tissues of the body including the eye [Zifa and Fillion 1992; Hoyer et al. 1994; Tobin et al. 1988].

5HT is known to interact with at least seven major 5HT receptors ($5HT_{1-5}HT_7$), and additional subtypes within these families, to initiate intracellular biochemical events such as stimulation of second messengers (e.g. cAMP, inositol trisphosphate) eventually leading to the final biological response, for example, tissue contraction or hormone release, etc. [Hoyer et al. 1994; Martin et al. 1998]. Receptor subtypes within the $5HT_1$ family are negatively coupled to adenylyl cyclase (AC) and cause inhibition of cAMP production, while $5HT_4$, $5HT_6$, and $5HT_7$ receptors are positively coupled to AC and thus stimulate cAMP production when activated by 5HT [Martin et al. 1998]. The receptors in the $5 HT_2$ family are positively coupled to phospholipase C (PLC) and thus generate inositol phosphates and mobilize intracellular calcium when activated to mediate the effects of 5HT. The $5HT_3$ receptor is unique in that it couples to an ion channel which gates sodium, potassium, and calcium [Hoyer et al. 1994].

Known compounds exhibiting $5HT_2$ agonist activity have typically been designed to treat numerous central nervous system (CNS)-related conditions, particularly the treatment of obesity and depression, by activation of $5-HT_{2C}$ receptors. Thus, one desired property of known $5HT_2$ agonist compounds is that they easily penetrate the blood brain barrier. Compounds that readily penetrate the blood-brain-barrier by passive diffusion are generally lipophilic molecules, which do not contain polar functional groups that might impede this diffusion.

The utility of $5-HT_2$ agonists for controlling IOP in the monkey model of glaucoma has been established (WO 00/16761). $\alpha_2$ adrenoceptor agonists are also known for their use as IOP lowering agents. It is also known that compounds with $5-HT_{1A}$ agonist activity can be useful for the treatment of glaucomatous optic neuropathy (WO 0170223 A1). Until the present invention, no single compound possessing $5-HT_{2A}$ and/or $5-HT_{1A}$ agonist activity along with $\alpha_2$ adrenoceptor agonist activity has been known.

To treat ocular diseases, it is desirable to administer topically compositions that will remain in the ocular tissues and not cross the blood brain barrier and enter the CNS. What are needed are anti-glaucoma drugs with both IOP lowering potency and ocular neuroprotective activity. It is also desirable that such compounds would not have a propensity to cross the blood brain barrier.

SUMMARY OF THE INVENTION

The present invention overcomes these and other drawbacks of the prior art by providing benzodifuran imidazoline derivatives and benzofuran imidazoline compounds for lowering IOP and providing neuroprotection. More specifically, the present invention provides compounds of the formula:

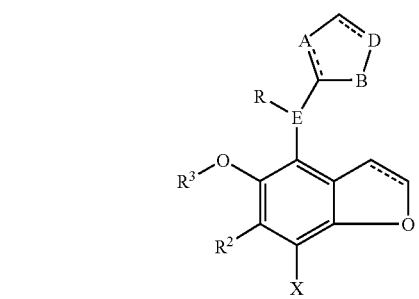

wherein A, B and D are independently chosen from either N or C, with the provision that at least one of A, B or D is N; E is C or N; R is H or $C_{1-4}$alkyl; $R^2$ and $R^3$ are independently H, $C_{1-3}$ alkyl, $C_{2-3}$ alkenyl, or $R^2$ and $R^3$ taken together can form a 5 or 6 member ring; hydrogen, halogen, $C_{1-4}$alkyl, or $CF_3$; and the dashed bond may be a single bond or a double bond; and pharmaceutically acceptable salts and solvates. Preferably the compound is 2-(8-bromo-benzo-[1,2-b;4,5-b']difuran-4-yl) imidazoline hydrochloride.

In another aspect, the present invention provides compositions containing the compounds described above. The compositions are most preferably in the form of topical ophthalmic formulations for delivery to the eye. The compounds of the invention may be combined with ophthalmologically acceptable preservatives, surfactants, viscosity enhancers, penetration enhancers, buffers, sodium chloride, and water to form an aqueous, sterile ophthalmic suspension or solution to form the compositions of the invention.

The compositions of the invention are preferably formulated as topical ophthalmic suspensions or solutions, with a pH of about 5 to 8. The compounds of the invention as described above will normally be contained in these formulations in an amount 0.01% to 5% by weight, but preferably in an amount of 0.1% to 2% by weight. Thus, for topical presentation 1 to 2 drops of these formulations would be delivered to the surface of the eye 1 to 4 times per day according to the routine discretion of a skilled clinician.

The present invention further provides a method of lowering intraocular pressure and providing ocular neuroprotection in a mammal by administering to a patient in need thereof a therapeutically effective amount of a composition comprising a compound having the structure as described above. In preferred embodiments, the composition can be administered locally to the eye (e.g., topically, intracamerally, or via an implant).

DETAILED DESCRIPTION PREFERRED EMBODIMENTS

Unexpectedly, it has been found that serotonergic compounds which possess agonist activity at $5HT_2$ receptors effectively lower and control elevated IOP and glaucoma. In addition, the compounds provide neuroprotective activity and are useful for treating persons suffering from ocular diseases associated with neuronal cell death. It has been found that serotonergic compounds which possess agonist activity at $5\text{-}HT_2$ receptors effectively lower and control normal and elevated IOP and are useful for treating glaucoma, see commonly owned co-pending application, PCT/US99/19888.

Compounds that act as agonists at $5\text{-}HT_2$ receptors are known and have shown a variety of utilities, primarily for disorders or conditions associated with the central nervous system (CNS). U.S. Pat. No. 5,494,928 discloses certain 2-(indol-1-yl)-ethylamine derivatives that are $5\text{-}HT_{2C}$ agonists for the treatment of obsessive compulsive disorder and other CNS derived personality disorders. U.S. Pat. No. 5,571,833 discloses tryptamine derivatives that are $5\text{-}HT_2$ agonists for the treatment of portal hypertension and migraine. U.S. Pat. No. 5,874,477 discloses a method for treating malaria using $5\text{-}HT_{2A/2C}$ agonists. U.S. Pat. No. 5,902,815 discloses the use of $5\text{-}HT_{2A}$ agonists to prevent adverse effects of NMDA receptor hypo-function. WO 98/31354A2 discloses $5\text{-}HT_{2B}$ agonists for the treatment of depression and other CNS conditions. Agonist response at the $5\text{-}HT_{2A}$ receptor is reported to be the primary activity responsible for hallucinogenic activity, with some lesser involvement of the $5\text{-}HT_{2C}$ receptor possible (Fiorella et al. 1995).

Serotonergic $5\text{-}HT_{1A}$ agonists have been reported as being neuroprotective in animal models and many of these agents have been evaluated for the treatment of acute stroke among other indications. This class of compounds has been disclosed for the treatment of glaucoma (lowering and controlling IOP), see e.g., WO 98/18458 and EP 0771563A2. Osborne et al. teach that 8-hydroxydipropylaminotetralin (8-OH-DPAT) (a $5\text{-}HT_{1A}$ agonist) reduces IOP in rabbits (Osborne et al. 1996). Wang et al. disclose that 5-methylurapidil, an $\alpha_{1A}$ antagonist and $5\text{-}HT_{1A}$ agonist lowers IOP in the monkey, but due to its $\alpha_{1A}$ receptor activity (Wang et al. 1997; Wang et al. 1998). Also, $5\text{-}HT_{1A}$ antagonists are disclosed as being useful for the treatment of glaucoma (elevated IOP) (e.g. WO 92/0338). Furthermore, DeSai et al. (WO 97/35579) and Macor et al. (U.S. Pat. No. 5,578,612) disclose the use of $5\text{-}HT_1$ and $5\text{-}HT_{1\text{-}like}$ agonists for the treatment of glaucoma (elevated IOP). These anti-migraine compounds are $5\text{-}HT_{1B,D,E,F}$ agonists, e.g., sumatriptan and naratriptan and related compounds.

The present invention provides compounds possessing $\alpha_2$ adrenoceptor agonist activity along with $5\text{-}HT_{2A}$ and $5\text{-}HT_{1A}$ activities having the general structure of Formula I.

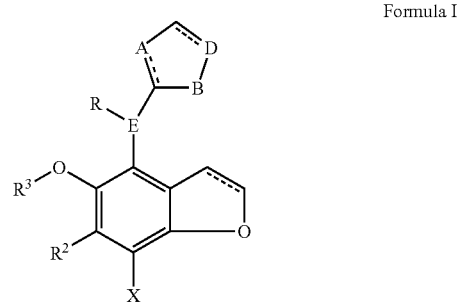

Formula I wherein A, B and D are independently chosen from ether N, C, with the provision that at least one of A, B or D is N; E is C or N; R is H, $C_{1\text{-}4}$alkyl; $R^2$ is H, $C_{1\text{-}3}$ alkyl, or $C_{2\text{-}3}$ alkenyl; $R^3$ is H, $C_{1\text{-}3}$ alkyl, or $C_{2\text{-}3}$ alkenyl; or $R^2$ and $R^3$ taken together can form a 5 or 6 member ring; X is chosen from hydrogen, halogen, $C_{1\text{-}4}$alkyl, $CF_3$; the dashed bond indicates that either a single bond or a double bond can exist at this bond location; and pharmaceutically acceptable salts and solvates. In preferred embodiments, the compound of the invention is 2-(8-bromo-benzo-[1.2-b;4,5-b']difuran-4-yl) imidazoline hydrochloride.

ES 323985 discusses that oxymetazoline is currently used for nasal de-congestion and in an ophthalmic solution to relieve redness of the eye. Although ES 323985 does discuss IOP lowering activity for oxymetazoline, it does not discuss the use of oxymetazoline for lowering IOP and ocular neuroprotection. Moreover, oxymetazoline is not a benzofuran as it lacks the furan substituent(s) and/or the ether substituent (Wang et al. 1993). Further, none of the claimed compounds are disclosed in ES 323985 or Wang.

It is recognized that compounds of Formula I can contain one or more chiral centers. This invention contemplates all enantiomers, diastereomers and, mixtures thereof.

In the above definitions, the total number of carbon atoms in a substituent group is indicated by the $C_{i\text{-}j}$ prefix where the numbers i and j define the number of carbon atoms; this definition includes straight chain, branched chain, and cyclic alkyl or (cyclic alkyl)alkyl groups.

It is important to recognize that a substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

The compounds of the invention can be administered systemically or locally to the eye (e.g., topically, intracamerally, or via an implant). The compounds are preferably incorporated into topical ophthalmic formulations for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Additionally, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like, according to the published formulations for analogous ophthalmic preparations; preservatives and tonicity agents can be incorporated.

The compounds of the invention are preferably formulated as topical ophthalmic suspensions or solutions, with a pH of about 5 to 8. The compounds will normally be contained in these formulations in an amount 0.01% to 5% by weight, but preferably in an amount of 0.1% to 2% by weight. Thus, for topical presentation 1 to 2 drops of these formulations would be delivered to the surface of the eye 1 to 4 times per day according to the routine discretion of a skilled clinician.

The compounds can also be used in combination with other IOP lowering agents, such as, but not limited to, β-blockers, prostaglandins, carbonic anhydrase inhibitors, and miotics. The compounds can also be used in combination with other agents useful for treating glaucoma, such as, but not limited to, calcium channel blockers and NMDA antagonists. These agents may be administered topically, but usually systemically.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthetic Scheme for 2-(8-bromo-benzo-[1,2-b;4,5-b']difuran-4-yl) imidazoline hydrochloride Examples of the compounds of this invention may be prepared by the synthetic route describe by Scheme 1. Briefly, the commercially available bis ethanol ether is treated with thionyl chloride in the presence of a organic base preferably pyridine in a solvent such as methylene chloride to form 2. The halogenated ether 2 is brominated using bromine in the presence of a Lewis acid such as zinc chloride in a solvent such as acetic acid to give compound 3. The di-bromide is cyclized to 4 with n-butyl lithium in a solvent such as dioxane or tetrahydrofuran maintained at a temperature of −40 to 0° C. Formylation with dichloromethyl methyl ether in the presence of stannic chloride in an inert solvent such as methylene chloride provides 5. Reduction of the aldehyde with sodium borohyride in a solvent such as ethanol or isopropyl alcohol yields the alcohol 6. The alcohol is converted to the chloride 7 by treatment with thionyl chloride in the presence of pyridine in a solvent such as methylene chloride. The nitrile 8 is formed by reacting 7 with sodium cyanide in a solvent such as DMSO at a temperature of 40–80° C. Bromination of the nitrile with a mixture of bromine and acetic acid at temperatures 0 to 20° C. yields compound 9. Reduction of the bis dihydrofuran with 2,3-dichloro-5,6-dicyano-1,4-benzoquinone (DDQ) in a solvent such as dioxane at temperatures between 80 to 130° C. yields compound 10. Treatment of the nitrile 10 with hydrogen chloride gas in a solution of ethanol and ether provides the imino ester, 11. Cyclization of the imino ester with ethylenediamine in ethanol and conversion of the product to the hydrochloride salt using a solution of hydrogen chloride in ethanol yields imidazoline benzodifuran 12.

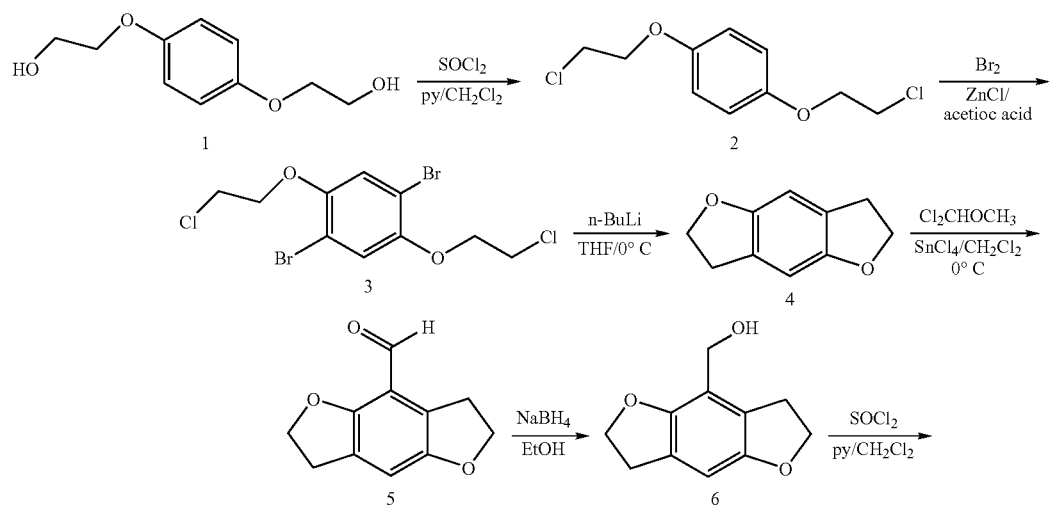

Scheme 1

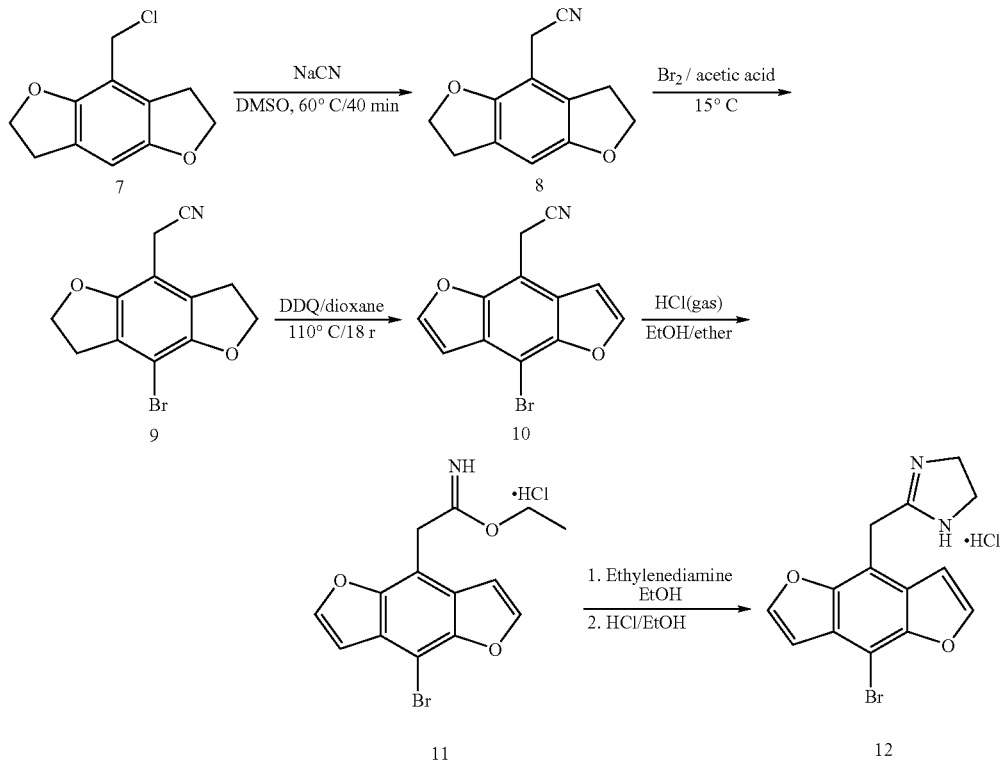

Example 2

2-(8-bromo-benzo-[1,2-b;4,5-b']difuran-4-yl) imidazoline hydrochloride 2-(8-Bromo-benzo-[1,2-b;4,5-b']difuran-4-yl) imidazoline hydrochloride was prepared by the multi-step procedure described below.

Step A: 1,4-Bis(2chloroethoxy)benzene

Bis(2-hydroxyethyl)hydroquinone (50 g, 0.25 mol) was dissolved in 500 ml of $CH_2Cl_2$ and cooled to 0° C., pyridine (48 ml, 0.6 mol) and thionyl chloride (41 ml, 0.58 ml) were added dropwise such that the temperature did not exceed 5° C. The mixture was allowed to warm to room temperature and was stirred over night. The solvent volume was reduced to 150 ml. Aqueous 2N HCl (150 ml) was added slowly and the layers were separated. The aqueous layer was extracted with $CH_2Cl_2$ (3×100 ml). The combined organic layer was washed with 2N HCl (150 ml), saturated NaCl solution (150 ml), dried over anhydrous $MgSO_4$, filtered and evaporated to a white solid. Recrystallization from is ethanol afforded a white solid (73 g). CIMS m/z 236 $(M+H)^+$.

Step B: 1,4-Bis(2-chloroethoxy)-2,5-dibromobenzene 1,4-Bis(2-chloroethoxy)benzene (40 g, 0.17 mol) was suspended in acetic acid (400 ml) and zinc chloride (56 g, 0.41 mol) was added. Bromine (57, 0.36 mol) dissolved in acetic acid (80 ml) was added dropwise to the suspension over 1.5 h. The reaction was stirred at room temperature over night, during which time a precipitate formed. The solids were filtered, washed with acetic acid and ethanol and dried. A crystalline white product was obtained (45 g). CIMS m/z 393 $(M+H)^+$.

Step C: 2,3,6,7-Tetrahydrobenzol-[1,2-b;4,5-b']difuran

A solution of 1,4-Bis(2-chloroethoxy)-2,5-dibromobenzene (15 g, 0.036 mol) in dry THF (300 ml) was cooled to 0° C. under nitrogen. A solution of 2.5 M n-butyl lithium in hexane (30 ml, 0.075 mol) was added through a syringe very quickly to the well stirred solution. The reaction mixture was stirred at 0° C. for 10 min, and the solvent was removed in vacuo. The residue was partitioned between ether (300 ml) and water (200 ml). The organic layer was washed with water (200 ml), dried over $MgSO_4$ and filtered. The solution was evaporated on a rotary evaporator until solids formed. The solids were filtered and dried to afford 4.3 g of 2,3,6,7-tetrahydrobenzol[1,2-b;4,5-b']difuran. CIMS m/z 163 $(M+H)^+$.

Step D: 4-Formyl-2,3,6,7-tetrahydrobenzol[1,2-b;4,5-b']difuran

Tin(IV) chloride (11.7 ml, 0.1 mol) was added through a syringe to a solution of 2,3,6,7-tetrahydrobenzol[1,2-b;4,5-b']difuran (12.6 g, 0.078 mol) in 300 ml of dry $CH_2Cl_2$ at 0° C. under $N_2$, and the mixture was stirred for 5 min. Dichloromethyl methyl ether (7 ml, 0.078 mol) in 20 ml of $CH_2Cl_2$ was added into the mixture dropwise over a 10 min period. After the mixture was stirred for 30 min, the reaction was quenched by the addition of 100 ml of ice water. The aqueous layer was extracted with $CH_2Cl_2$ (2×100 ml). The organic layers were combined and the resulting solution was washed with 3N HCl (3×150 ml), H$_2$O (200 ml), and a saturated NaCl solution (200 ml), dried over anhydrous MgSO$_4$, filtered and evaporated to a white solid. Recrystallization from CH$_2$Cl$_2$-hexane yielded 12.2 g of the product as a yellow solid. CIMS m/z 191 (M+H)$^+$.

Step E: 4-Hydroxymethyl-2,3,6,7-tetrahydrobenzol [1,2-b;4,5-b']difuran

A solution of NaBH$_4$ (2 g, 0.053 mol) in 40 ml of 90% EtOH was added dropwise to a solution of 4-Formyl-2,3,6,7-tetrahydrobenzol[1,2-b;4,5-b']difuran (10 g, 0.053 mol) in 200 ml of EtOH. The solution was stirred at room temperature for 30 min and at 60° C. for 10 min. After cooling to 0° C., 5 ml of 1N HCl was added and the solvent was evaporated. Ethyl acetate (80 ml) was added to the residue, and the resulting mixture was washed with H$_2$O (50 ml), saturated NaCl solution (50 ml), dried over anhydrous MgSO$_4$, filtered and evaporated to a residue. Chromatography of the residue on silica gel, eluting with 30% ethyl acetate in hexane, gave 7.5 g of 4-hydroxymethyl-2,3,6,7-tetrahydrobenzol[1,2-b;4,5-b']difuran as a white solid. CIMS m/z 193 (M+H)$^+$.

Step F: 4-Chloromethyl-2,3,6,7-tetrahrdrobenzol[1,2-b;4,5-b']difuran

Pyridine (4 ml, 0.05 mol) was added to a solution of 4-hydroxymethyl-2,3,6,7-tetrahrdrobenzol[1,2-b;4,5-b']difuran (4 g, 0.021 mol) in 50 ml of CH$_2$Cl$_2$ and the mixture was cooled to 0° C. Thionyl chloride (3.5 ml, 0.048 mol) was added dropwise. The resulting mixture was allowed to warm to room temperature and stirred for 6 h. After cooling, the mixture was washed with 1 N NaOH (2×50 ml), saturated NaCl solution (100 ml), dried over anhydrous MgSO$_4$, filtered and evaporated to a residue. Chromatography of the residue on silica gel, eluting with 10% ethyl acetate in hexane, gave 2.5 g of the product as a white solid. CIMS m/z 211 (M+H)$^+$.

Step G: 4-Acetonitrile-2,3,6,7-tetrahrdrobenzol[1,2-b;4,5-b']difuran

4-Chloromethyl-2,3,6,7-tetrahydrobenzol[1,2-b;4,5-b']difuran (2 g, 0.01 mol) in 20 ml of DMSO was added dropwise to a solution of sodium cyanide (0.75 g, 0.015 mol) in 20 ml of DMSO at 70° C. The mixture was stirred at 70° C. for 40 min. After cooling, 50 ml of ice-water was added. The precipitate formed was filtered, washed with water and dried giving white solid 8 (1.4 g). CIMS m/z 202 (M+H)$^+$.

Step H: 4-Acetonitrile-8-bromo-2,3,6,7-tetrahrdrobenzol[1,2-b;4,5-b']difuran

Bromine (1.1 g, 0.007 mol) in 10 ml of acetic acid was added dropwise to a suspension of 4-acetonitrile-2,3,6,7-tetrahydrobenzol[1,2-b;4,5-b']difuran (1.4 g, 0.007 mol) in 20 ml of acetic acid at 15° C. The mixture was stirred at 15° C. for 15 min. The precipitate formed was filtered, washed with acetic acid and ethanol and dried to yield 1.4 g of the product as a white solid. CIMS m/z 281 (M+H)$^+$.

Step I: 4Acetonitrile-8-bromo-[1,2-b;4,5-b']difuran

A solution of DDQ in 70 ml of dioxane was added dropwise to a solution of 4-acetonitrile-8-bromo-2,3,6,7-tetrahrdrobenzol[1,2-b;4,5-b']difuran (1.4 g, 0.005 mol) in 70 ml of dioxane. The mixture was stirred at reflux for 24 h. After cooling, the precipitate that formed was filtered and washed with dioxane. The filtrate was evaporated to a residue, which was subjected to chromatography on silica gel, eluting with 10% ethyl acetate in hexane, to yield 0.61 g of 10 as a white solid. CIMS m/z 277 (M+H)$^+$, mp 169–170° C.

Step J: Ethyl (8-bromo-[1,2-b;4,5-b']difuran-4-yl) acetimidate hydrochloride

An excess of dry HCl gas was passed through a solution of 4-acetonitrile-8-bromo-[1,2-b;4,5-b']difuran (0.6 g, 0.0022 mol) in 50 ml of anhydrous ether and 3 ml of absolute ethanol at 0° C. The resulting mixture was allowed to stirred at 0° C. for 1 h and at room temperature over night. The white solid formed was collected by filtration, washed with ether and dried to give white crystal of the product (0.6 g). ESMS m/z 323 (M+H)$^+$, mp 239–240° C. (dec).

Step K: 2-(8-Bromo-benzo-[1,2-b;4,5-b']difuran-4-yl)imidazoline hydrochloride

A solution of ethylenediamine (0.8 ml, 0.012 mol) in absolute ethanol (5 ml) was added dropwise to a suspension of ethyl (8-bromo-[1,2-b;4,5-b']difuran-4-yl)acetimidate hydrochloride (0.54 g, 0.0015 mol) in absolute ethanol (50 ml) at 0° C. The resulting mixture was stirred at 0° C. for 1 h and then refluxed for 20 min. The solvent was evaporated and the residue was dissolved in 20 ml of ethanol. A solution of 1N HCl in ether was added to the solution above to reach a pH of 3 and the mixture was stirred at room temperature overnight. The white solid that formed (0.4 g) was filtered, dried and recrystallized from MeOH/ether to afford the product (0.32 g). APCIMS m/z 320 (M+H)$^+$, mp 264–265° C. (dec). $^1$H NMR (CDCl$_3$) □ 8.21–8.19 (s, 2H), 7.43 (s, 1H), 7.08 (s, 1H), 4.47 (s, 2H), 3.83 (s, 4H), 3.32 (s, 2H), $^{13}$C NMR (CDCl$_3$) □ 168.10 (C), 149.45 (C), 148.49 (C), 147.99 (CH), 147.63 (CH), 126.26 (C), 126.13 (C), 106.64 (CH), 106.53 (CH), 106.24 (C), 93.40 (C), 44.24 (CH$_2$), 24.15 (CH$_2$). Anal. (C$_{14}$H$_{11}$BrN$_2$O$_2$ HCl), Cal: C, 47.29%; H, 3.40%; N, 7.87%; found: C, 47.05%; H, 3.56%; N, 7.98%.

Example 3

5-HT$_2$ Receptor Binding Assay

In order to determine the relative affinities of serotonergic compounds at the 5-HT$_2$ receptors, their ability to compete for the binding of the agonist radioligand [$^{125}$I]DOI to brain 5-HT$_2$ receptors is determined as described below with minor modification of the literature procedure (Johnson et al. 1987). Aliquots of post mortem rat cerebral cortex homogenates (400 μl) dispersed in 50 mM TrisHCl buffer (pH 7.4) are incubated with [$^{125}$I]DOI (80 pM final) in the absence or presence of methiothepin (10 μM final) to define total and non-specific binding, respectively, in a total volume of 0.5 ml. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program (Bowen et al. 1995) to determine the compound affinity parameter. The concentration of the compound needed to inhibit the [$^{125}$I]DOI binding by 50% of the maximum is termed the $IC_{50}$ or $K_i$ value. Compounds are considered to possess high affinity for the 5-HT$_2$ receptor if their $IC_{50}$ or $K_i$ values are $\leq$50 nM.

Example 4

5-HT$_2$ Functional Assay: Phosphoinositide (PI) Turnover Assay

The relative agonist activity of serotonergic compounds at the 5-HT$_2$ receptor can be determined in vitro using the ability of the compounds to stimulate the production of [$^3$H]inositol phosphates in [$^3$H]myo-inositol-labeled A7r5 rat vascular smooth muscle cells by their ability to activate the enzyme phospholipase C. These cells are grown in culture plates, maintained in a humidified atmosphere of 5% $CO_2$ and 95% air and fed semi-weekly with Dulbecco's modified Eagle medium (DMEM) containing 4.5 g/l glucose and supplemented with 2 mM glutamine, 10 µg/ml gentamicin, and 10% fetal bovine serum. For the purpose of conducting the phosphoinositide (PI) turnover experiments, the A7r5 cells are cultured in 24-well plates as previously described (Griffin et al. 1998). Confluent cells are exposed for 24–30 hrs to 1.5 µCi [$^3$H]-myo-inositol (18.3 Ci/mmol) in 0.5 ml of serum-free medium. Cells are then rinsed once with DMEM/F-12 containing 10 mM LiCl prior to incubation with the test agent (or solvent as the control) in 1.0 ml of the same medium for 1 hr at 37° C., after which the medium is aspirated and 1 ml of cold 0.1 M formic acid added to stop the reaction. The chromatographic separation of [$^3$H]-inositol phosphates ([$^1$H]-IPs) on an AG-1-X8 column is performed as previously described (Griffin et al. 1998) with sequential washes with $H_2O$ and 50 mM ammonium formate, followed by elution of the total [$^3$H]-IPs fraction with 1.2 M ammonium formate containing 0.1 M formic acid. The eluate (4 ml) is collected, mixed with 15 ml scintillation fluid, and the total [$^3$H]-IPs determined by scintillation counting on a beta-counter. Concentration-response data are analyzed by the sigmoidal fit function of the Origin Scientific Graphics software (Microcal Software, Northampton, Mass.) to determine agonist potency ($EC_{50}$ value) and efficacy ($E_{max}$). Serotonin (5-HT) is used as a positive control (standard) agonist compound and the efficacy of test compounds is compared to that of 5-HT (set at 100%). The concentration of the compound needed to stimulate the production of [$^3$H]-IPs by 50% of the maximum response is termed the $EC_{50}$ value. Compounds are considered potent agonists if their $EC_{50}$ values in this functional assay are $\leq$1 µM and are considered full agonists if their efficacy is >80% of that of 5-HT.

The above procedures were used to generate the data shown in Table 1.

TABLE 1

5-HT2 Receptor Binding and Functional Data.

| Compound | $IC_{50}$, nM | $EC_{50}$, nM | Efficacy ($E_{max}$, %) |
|---|---|---|---|
| (R)-DOI | 0.46 | 277 | 82 |
| Example 1 | 4.0 | 967 | 30 |

Example 5

Acute IOP Response in Lasered (Hypertensive) Eyes of Conscious Cynomolgus Monkeys Intraocular pressure (IOP) can be determined with an Alcon Pneumatonometer after light corneal anesthesia with 0.1% proparacaine. Eyes are washed with saline after each measurement. After a baseline IOP measurement, test compound is instilled in one 30 µL aliquot to the right eyes only of nine cynomolgus monkeys. Vehicle is instilled in the right eyes of six additional animals. Subsequent IOP measurements are taken at 1, 3, and 6 hours.

Example 6

5-HT$_{1A}$ Receptor Binding Assay

5-HT$_{1A}$ binding studies were performed with human cloned receptors expressed in Chinese hamster ovary (CHO) cells using ($^3$H)8-OH DPAT as the ligand. Membranes from Chinese hamster ovary cells (CHO) expressing cloned 5-HT$_{1A}$ receptors (manufactured for NEN by Biosignal, Inc., Montreal, Canada) were homogenized in approximately 40 volumes of 50 mM Tris pH 7.4 for 5 sec. Drug dilutions were made using a Beckman Biomek 2000 robot (Beckman Instruments, Fullerton, Calif.). Incubations were conducted with membrane prep, test compounds, and 0.25 nM [$^3$H]8-OH-DPAT (NEN, Boston, Mass.) in the same buffer at 27° C. for 1 h. Assays were terminated by rapid vacuum filtration over Whatman GF/B glass fiber filters pre-soaked in 0.3% polyethyleneimine. Bound radioactivity was measured using liquid scintillation spectrometry. Data were analyzed using non-linear curve fitting programs (Sharif et al. 1999).

Ligand binding studies can also be run using membrane preparations from calf and rat brain (local source) and human cortex membranes. Specific brain regions were dissected out, homogenized in 10 volumes of 0.32 M sucrose and centrifuged for 10 min at 700×g. The resulting supernatant was centrifuged at 43,500×g for 10 min and the pellet re-suspended in 50 mM Tris-HCl (pH 7.7, 25° C.) using a 10 sec polytron treatment. Aliquots were stored at –140° C. To remove endogenous serotonin, the preps were incubated at 37° C. for 10 min prior to the experiment. Assay incubations were terminated by rapid filtration over Whatman GF/C filters using a Brandel cell harvester. $K_i$ values were calculated using the Cheng-Prusoff equation (De Vry et al. 1998).

Example 7

5-HT$_{1A}$ Functional Assays

The function of Compounds of the present invention can be determined using a variety of methods to assess the functional activity of 5-HT$_{1A}$ agonists. One such assay is performed using hippocampal slices from male Sprague-Dawley rats, measuring the inhibition of forskolin-stimated adenylate cyclase (Lopez-Rodriguez et al. 1999; Morin et al. 1991; De Vry et al. 1998). Rat hippocampal membranes were homogenized in 25 volumes of 0.3 M sucrose containing 1 mM EGTA, 5 mM EDTA, 5 mM dithiothreitol, and 20 mM Tris-HCl, pH 7.4 at 25° C. The homogenate was centrifuged for 10 m in at 1,000×g. The supernatant subsequently was centrifuged at 39,000×g for 10 min. The resulting pellet was re-suspended in homogenization buffer at a protein concentration of approximately 1 mg/ml and aliquots were stored at –140° C. Prior to use, the membranes were rehomogenized in a Potter-Elvehjem homogenizer. Fifty μl of the membrane suspension (50 μg protein) were added to an incubation buffer containing 100 mM NaCl, 2 mM magnesium acetate, 0.2 mM ATP, 1 mM cAMP, 0.01 mM GTP, 0.01 mM forskolin, 80 mM Tris-HCl, 5 mM creatine phosphate, 0.8 U/μl creatine phosphokinase, 0.1 mM IBMX, 1-2 μCi α-[$^{32}$P]ATP. Incubations with test compounds (10 min at 30° C.) were initiated by the addition of the membrane solution to the incubation mixture (prewarmed 5 min at 30° C.). [$^{32}$P]cAMP was measured according to the method of Salomon (Salomon 1979). Protein was measure using the Bradford assay (Bradford 1976).

Functional activity can also be determined in recombinant human receptors according to the method of Schoeffter et al. (1997). HeLa cells transfected with recombinant human 5-HT$_{1A}$ receptors were grown to confluence in 24-well plates. The cells were rinsed with 1 ml of Hepes-buffered saline (in mM) NaCl 130, KCl 5.4, CaCl$_2$, 1.8, MgSO$_4$ 0.8, NaH$_2$PO$_4$ 0.9, glucose 25, Hepes 20, pH 7.4, and phenol red 5 mg/l. The cells were labelled with 6 μCi/ml of [$^3$H] adenine (23 Ci/mmol, Amersham, Rahn AG, Zurich, Switzerland) in 0.5 ml of saline at 37° C. for 2 hr. The plates were subsequently rinsed twice with 1 ml of buffered saline containing 1 mM isobutylmethylxanthine. The cells were incubated for 15 min in 1 ml of this solution (37° C.) in the presence or absence of 10 μM forskolin and the test compound. The buffer was then removed and 1 ml of 5% trichloroacetic acid (TCA) containing 0.1 mM cAMP and 0.1 mM ATP was added to extract the samples. After 30 min at 4° C., the TCA extracts were subjected to chromatographic separation on Dowex AG 50W-X4 and alumina columns (Salomon 1991). Cyclic AMP production was calculated as the ratio [$^3$H]cAMP/([$^3$H]cAMP+[$^3$H]ATP).

TABLE 2

5-HT1A Receptor Binding and Functional Data.

| Compound | IC$_{50}$, nM | EC$_{50}$, nM | Efficacy (E$_{max}$, %) |
|---|---|---|---|
| (R)-8-OH-DPHAT | 0.52 | 2.6 | 102 |
| Example 1 | 6.4 | 110 | 94 |

Example 8

Alpha-2 Adrenergic Receptor Assay Methods

Cell culture. For the alpha-2A assays, HT29 human clonic adenocarcinoma cells were grown in McCoy's 5A Medium Modified supplemented with 10% (v/v) heat-inactivated fetal bovine serum in a humidified atmosphere of 5% CO$_2$/95% air. Cells were sub-cultured with 0.5% Trypsin/5.3 mM EDTA in 48 wells plates with confluence being reached in approximately 4 days. Growth medium was replaced with fresh medium, 24 hours before assay of confluent cells in order to avoid the nutrient exhaustion.

Cyclic AMP functional assays. Confluent cultures of HT29 cells were washed twice with 0.5 ml of 15 mM Hepes-buffered DMEM (DMEM/F12), then incubated with 0.5 ml DMEM/F12 containing 0.25 mM 3-Isobutyl-1-methyl-xanthine (IBMX) for 20 minutes. At the end of this period the appropriate serially diluted α2-adrenergic agonists was added and the cells were further incubated for 10 minutes. Then the appropriate concentration of forskolin (for HT29 cells 4 μM) was added and the cells were incubated for an additional 10 minutes. At the end of the incubation period the media was aspirated and 150 μl of 0.1 M acetic acid, pH 3.5 was added. The plates were incubated at 4o C for 20 minutes. Then 220 μl of 0.1 M sodium acetate, pH 11.5–12 was added. The plates were stored at −20° C. After this, a commercially available cAMP ELISA kit was used to quantify the amount of cAMP generated in the receptor assay. In all these alpha-2 receptor assays, an inhibition of cAMP production reflected a receptor-mediated process.

TABLE 3

Alpha2A Receptor Binding and Functional Data.

| Compound | EC$_{50}$, nM | Efficacy (E$_{max}$, %) |
|---|---|---|
| Brimonidine | 22 | 100 |
| Example 1 | 110 | 62 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.
United States Patents
U.S. Pat. No. 5,494,928
U.S. Pat. No. 5,571,833
U.S. Pat. No. 5,578,612
U.S. Pat. No. 5,874,477
U.S. Pat. No. 5,902,815
Foreign Patents and Published Applications
EP 0771563A2.
PCT/US99/19888
WO 92/0338
WO 97/35579
WO 98/18458
WO 98/31354 A2
WO 00/16761
WO 01/70223 A1
Other Publications
Bowen et al., TRENDS PHARMACOL. SCI., 16:413 (1995).
Bradford, ANAL. BIOCHEM 72:248–254 (1976).
De Vry et al., J. PHARM. EXPER. THER. 284(3):1082–1094 (1998).
Fiorella et al., PSYCHOPHARM. 121(3):347–356 (1995).
Griffin et al., J. PHARMACOL. EXPT. THER. 286(1):411–418 (1998).
Hoyer et al., PHARMACOL. REV. 46:157–203 (1994).
Johnson et al., NEUROPHARMACOLOGY, 26(12):1803–1806 (1987).

Lopez-Rodriguez et al., J. MED. CHEM. 42(1):3649 (1999).
Martin et al., TRENDS PHARMACOL. SCI. 19:2–4 (1998).
Morin et al., J. NEUROCHEM. 56(4):1114–1120 (1991).
Osborne, et al., OPHTHALMOLOGICA, 210:308–314 (1996).
Salomon, ADV. CYCLIC NUCLEOTIDE RES. 10:35–55 (1979).
Salomon, METHODS IN ENZYMOLOGY 195: 22–28 (1991).
Schoeffter et al. NEUROPHARM. 36:429–437 (1997).
Sharif et al., J. PHARMAC. PHARMACOL. 51: 685–694 (1999).
Tobin et al., J. NEUROSCI. 8:3713–3721 (1988).
Wang et al., ARCH. OPHTHALMOL. 111:535–538 (1993).
Wang, et al., CURRENT EYE RESEARCH, 16(8):769–775 (1997).
Wang et al., IVOS, 39(4), S488 (1998).
Zifa and Fillion, PHARMACOL. REV. 44:401–458 (1992).

We claim:
1. A compound of the formula:

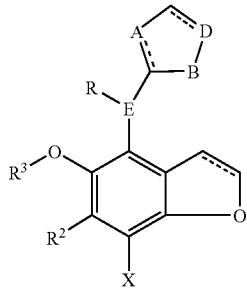

wherein A, B and D are independently chosen from either N or C, with the provision that at least
one of A, B or D is N;
E is C or N;
R is H or $C_{1-4}$alkyl;
$R^2$ and $R^3$ are independently H, $C_{1-3}$ alkyl, $C_{2-3}$ alkenyl, or $R^2$ and $R^3$ taken together can form a 5 or 6 member ring;
X is hydrogen, halogen, $C_{1-4}$alkyl, or $CF_3$; and
the dashed bond may be a single bond or a double bond; and pharmaceutically acceptable salts and solvates.

2. The compound of claim 1, wherein the compound is 2-(8-bromo-benzo-[1, 2-b;4,5-b']difuran-4-yl) imidazoline hydrochloride.

3. A method for lowering intraocular pressure comprising administering to a patient in need thereof a therapeutically effective amount of a composition comprising a compound of the formula:

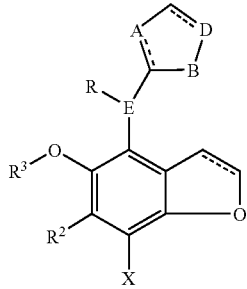

wherein A, B and D are independently chosen from either N or C, with the provision that at least one of A, B or D is N;
E is C or N;
R is H or $C_{1-4}$alkyl;
$R^2$ and $R^3$ are independently H, $C_{1-3}$ alkyl, $C_{2-3}$ alkenyl, or $R^2$ and $R^3$ taken together can form a 5 or 6 member ring;
X is hydrogen, halogen, $C_{1-4}$alkyl, or $CF_3$; and
the dashed bond may be a single bond or a double bond; and pharmaceutically acceptable salts and solvates.

4. The method of claim 3, wherein the compound is 2-(8-bromo-benzo-[1, 2-b;-4,5-b']difuran-4-yl) imidazoline hydrochloride.

5. A composition for lowering and controlling normal or elevated intraocular pressure, comprising a compound of the formula:

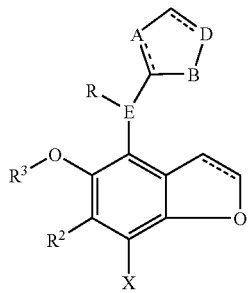

wherein A, B and D are independently chosen from either N or C, with the provision that at least one of A, B or D is N;
E is C or N;
R is H or $C_{1-4}$alkyl;
$R^2$ and $R^3$ are independently H, $C_{1-3}$ alkyl, $C_{2-3}$ alkenyl, or $R^2$ and $R^3$ taken together can form a 5 or 6 member ring;
X is hydrogen, halogen, $C_{1-4}$alkyl, or $CF_3$; and
the dashed bond may be a single bond or a double bond; and pharmaceutically acceptable salts and solvates.

6. The composition of claim 5, wherein the compound is 2-(8-bromo-benzo-[1,2-b;4,5-b'] difuran-4-yl) imidazoline hydrochloride.

7. The composition of claim 6, further comprising ophthalmologically acceptable preservatives.

8. The composition of claim 6, further comprising ophthalmologically acceptable surfactants.

9. The composition of claim 6, further comprising an agent to increase viscosity.

10. The composition of claim 9, wherein the agent is selected from the group consisting of hydroxymethylcellulose, hydroxyethylcellulose, hydroxypropylmethylcellulose, methylcellulose, and polyvinylpyrrolidone.

11. The composition of claim 6, further comprising ophthalmologically acceptable preservatives, ophthalmologically acceptable surfactants and at least one agent to increase viscosity.

12. The composition of claim 6, further defined as a topical ophthalmic suspension or solution having a pH of about 5 to about 8.

13. The composition of claim 12, wherein the concentration of the compound is from 0.01% to 5% by weight.

14. The composition of claim 13, wherein the composition of the compound is from 0.25% to 2% by weight.

* * * * *